US006662628B2

(12) United States Patent
Horváth et al.

(10) Patent No.: US 6,662,628 B2
(45) Date of Patent: Dec. 16, 2003

(54) METHOD FOR DETERMINING THE PROPORTION OF A GAS CONSTITUENT CONTAINED IN A GAS MIXTURE

(75) Inventors: Jenö Horváth, Stuttgart (DE); Werner Schwarzbäcker, Eglfing (DE)

(73) Assignee: Convotherm Elektrogeräte GmbH, Eglfing (DE)

( * ) Notice: Subject to any disclaimer, the term of this patent is extended or adjusted under 35 U.S.C. 154(b) by 0 days.

(21) Appl. No.: 10/181,533

(22) PCT Filed: Jan. 18, 2001

(86) PCT No.: PCT/EP01/00561
§ 371 (c)(1),
(2), (4) Date: Jul. 18, 2002

(87) PCT Pub. No.: WO01/53797
PCT Pub. Date: Jul. 26, 2001

(65) Prior Publication Data
US 2003/0000284 A1 Jan. 2, 2003

(30) Foreign Application Priority Data
Jan. 20, 2000 (DE) .......................................... 100 02 309

(51) Int. Cl.⁷ .................................................. G01N 7/00
(52) U.S. Cl. ....................... 73/29.01; 73/23.2; 73/31.01; 73/861.22
(58) Field of Search .............................. 73/23.2, 29.01, 73/31.01, 861.22; 426/99

(56) References Cited

U.S. PATENT DOCUMENTS

| | | | | |
|---|---|---|---|---|
| 5,187,972 A | * | 2/1993 | DeFriez | 73/23.2 |
| 5,828,200 A | * | 10/1998 | Ligman et al. | 318/807 |
| 6,159,360 A | * | 12/2000 | Gerteis et al. | 210/103 |
| 6,470,597 B1 | * | 10/2002 | Stipp | 34/422 |

FOREIGN PATENT DOCUMENTS

| | | | |
|---|---|---|---|
| DE | 2 259 459 | 6/1974 | G01N/9/36 |
| DE | 42 06 845 | 9/1993 | G01N/9/36 |
| DE | 196 11 528 | 7/1997 | G01N/11/14 |

* cited by examiner

Primary Examiner—Hezron Williams
Assistant Examiner—Andre' K. Jackson
(74) Attorney, Agent, or Firm—Cohen, Pontani, Lieberman & Pavane

(57) ABSTRACT

An asynchronous motor is used in the process for determining the proportion of a gas constituent, especially water vapor, contained in a gas mixture. The asynchronous motor drives a delivery device for circulating the gas mixture that is used for treating foodstuffs. The difference between the rotational speed, which occurs while the delivery device is driven, and the synchronous rotational speed, i.e. the slip, is used as a measure for the sought proportion of the gas constituent at respectively established pressure and temperature values of the gas mixture.

2 Claims, 2 Drawing Sheets

METHOD FOR DETERMINING THE PROPORTION OF A GAS CONSTITUENT CONTAINED IN A GAS MIXTURE

PRIORITY CLAIM

This is a U.S. national stage of application No. PCT/EP01/00561, filed on Jan. 18, 2001. Priority is claimed on that application and on the following application(s): Country: Germany, Application No.: 100 02 309.6, Filed: Jan. 20, 2000.

BACKGROUND OF THE INVENTION

1. Field of the Invention

The invention relates to a method for determining the proportion of a gas component, in particular steam, in a gas mixture, using a drive-device-driven transport device for the gas mixture.

2. Description of the Related Art

To determine gas components in a gas mixture, usually sensors are used. The higher the temperature of the gas, and the more the sensors are exposed to impurities, the more fault-susceptible these sensors become.

DE 42 06 845 C2 discloses, starting from the known data of a gas mixture, determining the proportion of a gas component, for example steam, by disposing auxiliary blades on a fan for generating pressure differences, in which case, then, from the pressure difference at differing measuring points, the proportion of steam can then be concluded. Since these pressure differences are only very small, pressure difference measuring instruments must be used which have particular sensitivity and accuracy of measurement.

DE 22 59 459 discloses, in the conditioning of textiles, measuring the steam content of the mixture at regular intervals and correcting it if there is a deviation from the preset value. To measure the mixing ratio of steam and air, a fan is used in a measuring apparatus, the total pressure produced or the power consumption of the fan being determined in this measuring apparatus and this value being used to control the mixing ratio.

SUMMARY OF THE INVENTION

It is an object of the invention, with a cooking apparatus for treating foods, in a simple manner, that is to say using the existing drive apparatus and transport apparatus, to determine the proportion of a gas component, in particular steam, in the gas mixture and thus obtain an index for the moisture.

This object is achieved by the measures specified in claim 1.

In this concept of the solution, the fact is exploited that the density of the gas mixture essentially determines the output of the transport device, while the dynamic viscosity of the gas mixture is decisive for the friction losses of the transport device with the gas mixture. If the densities and/or dynamic viscosities of the gas components differ, depending on the composition of the gas mixture, a density and dynamic viscosity which are characteristic for the gas mixture result. In the inventive method, it is then only necessary to record, from appropriate tables available in the literature, the values for density and dynamic viscosity of the two components of a gas mixture in each case at specified pressure and temperature values, as a result for any desired mixing ratio of two components the resultant density and resultant dynamic viscosity of this mixture are obtained. The greater the density and dynamic viscosity of the gas mixture, the more power must a transport device apply under otherwise constant operating parameters.

A preferred use of the inventive method is that the established parameter is used as control parameter for influencing the composition of the gas mixture, in particular for moisture control of the treatment medium in apparatuses for treating foods. Since in the case of such cooking apparatuses, for example hot air steamers, the temperature in the cooking chamber is determined in any case as an essential state parameter and the atmospheric pressure is ubiquitous pressure information, the invention leads to a particularly simple substantially fault-free economic and in addition still relatively exact method for measuring the composition of the gas mixture of air and steam, and thus the moisture in the cooking apparatus.

DETAILED DESCRIPTION OF THE PRESENTLY PREFERRED EMBODIMENTS

Figure 1:
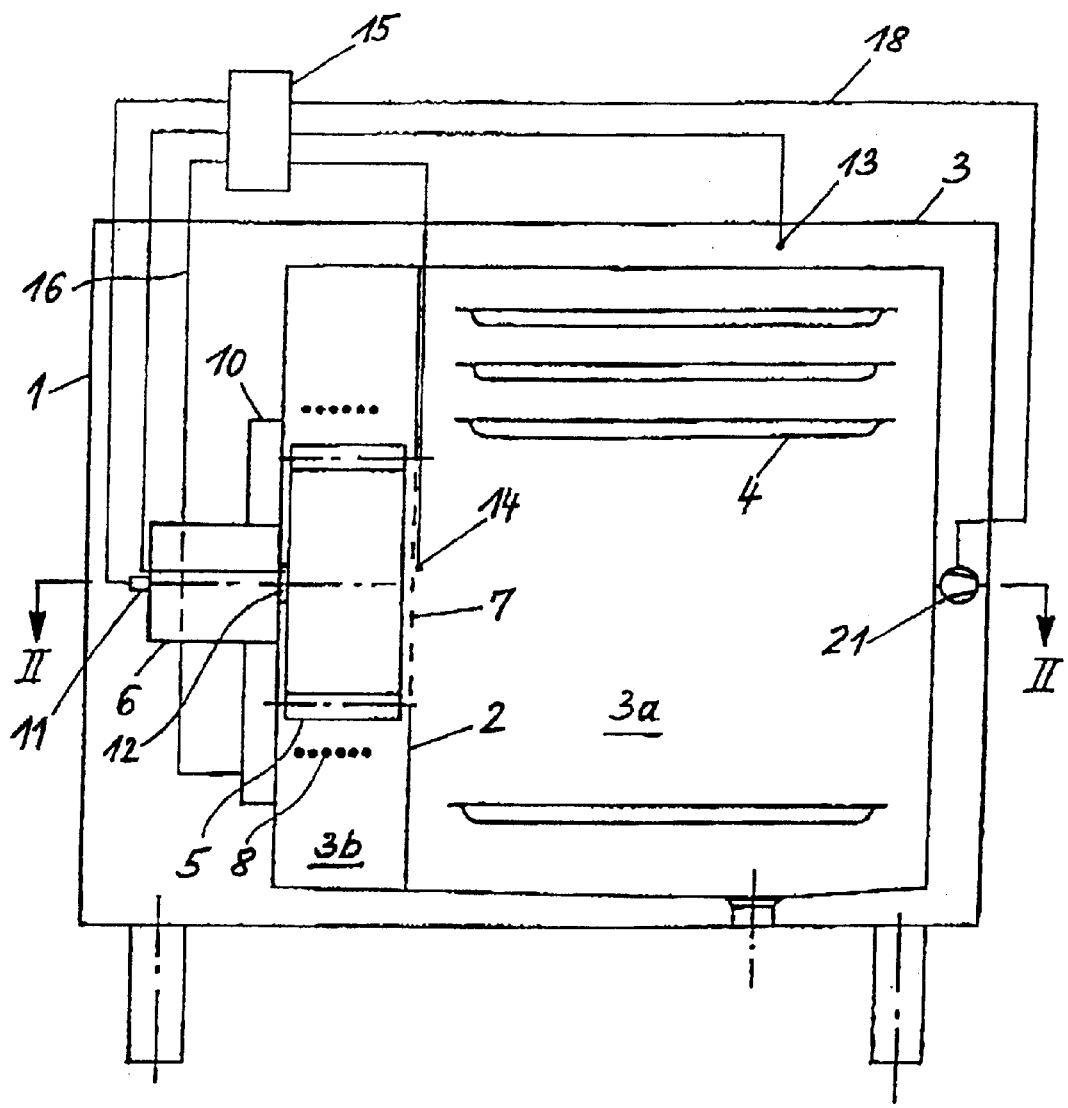
FIG. 1: shows a section through a cooking apparatus equipped with data analysis for carrying out the method.
Figure 2:
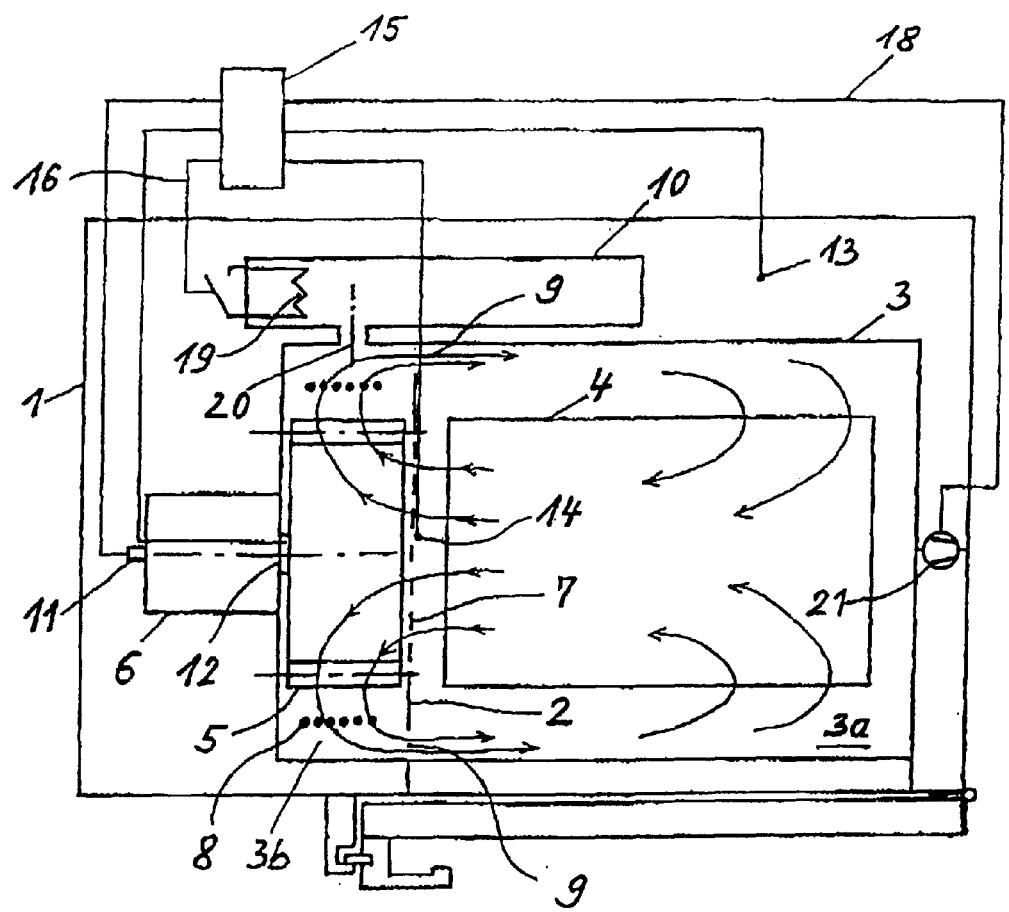
FIG. 2: shows a section through the line II—II in FIG. 1.

As can be seen in FIGS. 1 and 2, in a housing 1 of a cooking apparatus, the interior 3 is divided by a partition 2 into a cooking chamber 3a and an operating chamber 3b. In the cooking chamber, gratings 4 for holding food to be treated are provided on a rack which is not shown. In the operating chamber 3b, a fan 5 can be driven by a drive motor 6 that takes in the gas mixture or medium present in the cooking chamber 3a via a mesh 7 and forces this medium back into the cooking chamber via a heater 8 and slots 9. A steam generator 10 supplies the steam necessary to generate a steam atmosphere in the cooking chamber 3a.

To determine the proportion of dry air or the proportion of steam in the gas mixture, in the embodiment according to FIGS. 1 and 2, a revolution counter 11 and a device 12 for measuring the synchronous speed are provided on the drive motor 6. In addition, a pressure sensor 13 and, within the cooking chamber 3a, a temperature sensor 14 are disposed. Since the cooking chamber is not pressurized, apart from short-term and negligible pressure difference, the ambient atmospheric pressure always prevails. The atmospheric pressure need not therefore be measured in the cooking chamber, but can be determined somewhere at a particularly suitable position. Generally, a mean atmospheric pressure value corresponding to the elevation of the installation point of the apparatus is also sufficient in determining the composition of the gas mixture, so that in this case the pressure sensor is not necessary. The devices 11 to 14 are connected to a measured data processing and control apparatus 15, termed computer for short hereinafter. This computer can be disposed outside the apparatus 1, as indicated in FIGS. 1 and 2, but is preferably an integrated part of the existing equipment electronics. The usual equipment electronics can generally adopt the necessary functions of the computer 15 without needing to be substantially extended. The computer is programmable and contains the various material data, for example density and dynamic viscosity of dry and moist air at the various temperatures, for example in the temperature range from 20 to 300° C., and the relevant air pressures. In addition, this computer also contain characteristic motor data, so that when a defined slip is determined and when the temperature and pressure are determined the computer is able to determine the corresponding proportions of dry and moist air, which give the moisture in the cooking chamber. In addition, the computer can also contain a program in which defined preset values are stored for moisture at preset temperature values and pressure values. The proportions of the two gas components determined and the moisture thus determined is then compared with the appropriate preset value and, therefrom, via lines 16 and 18 appropriate control commands can then be transmitted to a heater 19 in the steam generator 10 and to a drying apparatus 21, in order to be able to set the composition of the internal atmosphere or cooking chamber atmosphere back to the desired value by supplying steam or removing moisture from the interior 3. The steam is supplied from a steam generator by activating the heater 19 via a slight overpressure of the steam generated through a connection line 20 between steam generator 10 and operating chamber 3b. The pressure equilibration in the interior is performed exactly as in the case of removal of moisture via connection tubes, which are not shown, between the interior and the surroundings. In the case of removal of moisture, a corresponding amount of gas mixture in the interior is replaced by the ambient air which is always very dry in relation to the cooking chamber atmosphere.

What is claimed is:

1. A method for controlling the proportion of a component in a gas mixture which is recirculated by means of a transport apparatus for treating foods in a cooking chamber, said method comprising driving said transport apparatus with an asynchronous motor having a known synchronous speed, determining the pressure and temperature of the gas mixture in the cooking chamber, measuring the rotational speed of the motor while it is driving said transport apparatus to recirculate the gas mixture, determining a difference between the rotational speed and the synchronous speed, said difference defining a slip, using said slip, said temperature, and said pressure to determine the proportion of said gas component in said gas mixture, comparing the determined proportion of said gas component to a desired value, and adjusting the amount of said component based on said comparison.

2. A method as in claim 1 wherein said gas component is steam, said adjustment being accomplished by one of adding steam to said gas mixture, and removing some of said gas mixture while adding air.

* * * * *